(12) United States Patent
Nojiri

(10) Patent No.: US 10,478,389 B2
(45) Date of Patent: *Nov. 19, 2019

(54) HAIR-DYE COMPOSITION

(71) Applicant: KAO CORPORATION, Tokyo (JP)

(72) Inventor: Masayoshi Nojiri, Chiba (JP)

(73) Assignee: KAO CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/316,631

(22) PCT Filed: Jun. 5, 2015

(86) PCT No.: PCT/JP2015/066281
§ 371 (c)(1),
(2) Date: Dec. 6, 2016

(87) PCT Pub. No.: WO2015/186817
PCT Pub. Date: Dec. 10, 2015

(65) Prior Publication Data
US 2017/0196791 A1   Jul. 13, 2017

(30) Foreign Application Priority Data

Jun. 6, 2014   (JP) .................. 2014-117912

(51) Int. Cl.
*A61Q 5/10* (2006.01)
*A61K 8/49* (2006.01)
(Continued)

(52) U.S. Cl.
CPC .......... *A61K 8/49* (2013.01); *A61K 8/19* (2013.01); *A61K 8/342* (2013.01); *A61K 8/41* (2013.01);
(Continued)

(58) Field of Classification Search
CPC . A61K 8/49; A61K 8/342; A61K 8/43; A61K 8/19; A61K 2800/4324;
(Continued)

(56) References Cited

U.S. PATENT DOCUMENTS

| 5,131,912 A | 7/1992 | Ehara et al. | |
|---|---|---|---|
| 2004/0019982 A1* | 2/2004 | Pratt | A61K 8/466 8/405 |
| 2010/0229314 A1* | 9/2010 | Takiguchi | A61K 8/442 8/405 |

FOREIGN PATENT DOCUMENTS

| EP | 2 606 873 | 6/2013 |
|---|---|---|
| EP | 2 606 875 | 6/2013 |

(Continued)

OTHER PUBLICATIONS

STIC Search Report (U.S. Appl. No. 15/316,648) dated May 23, 2017.*

(Continued)

*Primary Examiner* — Eisa B Elhilo
(74) *Attorney, Agent, or Firm* — Oblon, McClelland, Maier & Neustadt, L.L.P.

(57) ABSTRACT

A hair dye composition comprising the following components (A) and (B), in which the mass ratio of the component (B) to the component (A), (B)/(A), in a whole composition is 1 or more and 100 or less and the pH (25° C.) during application is 7.5 to 12:

(A): one or more azo dyes selected from the group consisting of the following (A-1), (A-2) and (A-3):

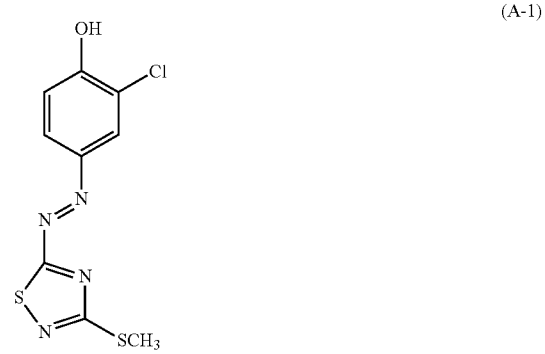

(A-1)

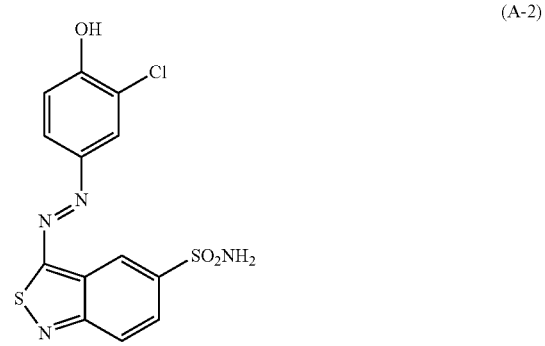

(A-2)

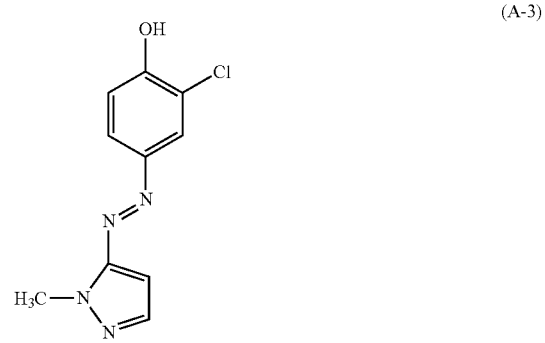

(A-3)

(B): at least one member selected from the group consisting of guanidine carbonate, guanidine hydrogen (Continued)

carbonate, sodium carbonate, sodium hydrogen carbonate, potassium carbonate, potassium hydrogen carbonate and lithium carbonate.

18 Claims, No Drawings

(51) Int. Cl.
  *A61K 8/41*  (2006.01)
  *A61K 8/19*  (2006.01)
  *A61K 8/34*  (2006.01)
  *A61K 8/43*  (2006.01)
  *A61K 8/72*  (2006.01)
  *A61Q 5/06*  (2006.01)

(52) U.S. Cl.
  CPC ............... *A61K 8/43* (2013.01); *A61K 8/494* (2013.01); *A61K 8/72* (2013.01); *A61Q 5/065* (2013.01); *A61Q 5/10* (2013.01); *A61K 2800/4322* (2013.01); *A61K 2800/4324* (2013.01); *A61K 2800/5426* (2013.01); *A61K 2800/596* (2013.01); *A61K 2800/805* (2013.01)

(58) Field of Classification Search
  CPC ...... A61K 2800/5426; A61K 2800/596; A61K 8/41; A61Q 5/10
  See application file for complete search history.

(56) References Cited

FOREIGN PATENT DOCUMENTS

| | | |
|---|---|---|
| EP | 2 883 530 | 6/2015 |
| EP | 2 883 531 A1 | 6/2015 |
| EP | 3 153 152 | 4/2017 |
| JP | 3-170413 A | 7/1991 |
| JP | 2003-342139 A | 12/2003 |
| JP | 2010-6804 A | 1/2010 |
| JP | 2010-24158 A | 2/2010 |
| WO | WO 2013/092903 A2 * 6/2013 ............... A61Q 5/10 |

OTHER PUBLICATIONS

International Search Report dated Aug. 11, 2015 in PCT/JP2015/066281 filed Jun. 5, 2015.

European Search Report in corresponding application No. 15803690.5, dated Nov. 30, 2017.

Y. Murata, Color Technology Handbook, Sogo Technical Center, 1990, pp. 202-207 (with partial English Translation).

* cited by examiner

HAIR-DYE COMPOSITION

CROSS REFERENCE TO RELATED APPLICATION

This application is a 371 of PCT/JP2015/066281, filed on Jun. 5, 2015, and claims priority to Japanese Patent Application No. 2014-117912, filed on Jun. 6, 2014.

FIELD OF THE INVENTION

The present invention relates to a hair dye composition and a method for dyeing hair using the composition.

BACKGROUND OF THE INVENTION

Hair dye compositions are classified depending upon the types of dyes to be used or the presence or absence of a melanin bleaching action. Typical examples of the hair dye compositions include a two-agent type oxidative hair dye composition consisting of a first agent containing an alkali agent, an oxidation dye and an optional direct dye such as a nitro dye and a second agent containing an oxidizing agent; and one-agent type non-oxidative hair dye composition containing a pH adjuster (acid or alkali) and at least one of direct dye such as an acid dye, a basic dye and a nitro dye.

As the direct dye to be used in these hair dye compositions, a dissociative azo dye is known which contains a dissociative proton in a molecule and displays a color by dissociation of the proton (for example, Patent Document 1).

[Patent Document 1] JP-A-2003-342139

SUMMARY OF THE INVENTION

The present invention provides a hair dye composition comprising the following components (A) and (B), in which the mass ratio of a component (B) to a component (A), (B)/(A), in a whole composition is 1 or more and 100 or less and the pH (25° C.) during application is 7.5 to 12:

(A): one or more azo dyes selected from the group consisting of the following (A-1), (A-2) and (A-3):

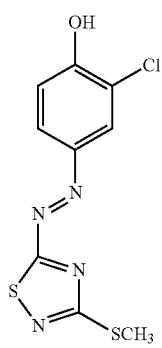

(A-1)

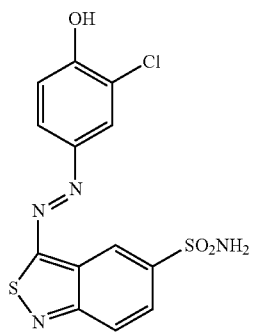

(A-2)

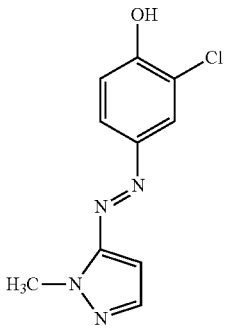

(A-3)

(B): at least one member selected from the group consisting of guanidine carbonate, guanidine hydrogen carbonate, sodium carbonate, sodium hydrogen carbonate, potassium carbonate, potassium hydrogen carbonate and lithium carbonate.

The present invention further provides a method for dyeing hair by applying the hair dye composition to the hair, allowing the composition to stand for 1 to 60 minutes and washing away the composition.

DETAILED DESCRIPTION OF THE INVENTION

In hair dyes containing direct dyes, almost all direct dyes color the hair by depositing onto a region of the hair from the surface to immediate vicinity thereof no matter which dosage form (mentioned above) the dyes have. The azo dye (dissociative azo dye) containing a dissociative proton(s) and proposed in Patent Literature 1 dissociates a proton(s) in an alkaline environment and an anion charge(s) is delocalized in a molecule, with the result that brilliant color is displayed; at the same time, mutual interaction with hair is produced. Due to the characteristic, the azo dye is a suitable direct dye to be used as a hair dye.

Recently, for obtaining glossy and resilient hair having a body, acidic shampoos have been widely used for washing hair and accordingly decoloration and color-change of hair colored with a hair dye containing such a dissociative azo dye became problems. The decoloration and color-change are considered to occur because an azo dye, which deposits on the hair and displays color as the result of dissociation of a dissociative proton(s) and delocalization of an anion charge(s), is protonated in the acidic condition, with the result that the molecule is neutralized to change color or the molecule becomes easily soluble to change the color tone of the hair.

The dissociative azo dye, since it is less soluble to a hair dye composition, tends to cause reprepicitation during production and storage. When such a hair dye is applied, the hair is frequently dyed nonuniformly due to the non-uniformity of the dye.

Thus, the present invention relates to a hair dye composition containing a dissociative azo dye improved in resistance to acidic treatment, and solubility to a hair dye composition.

Various types of alkaline agents were studied in order to overcome the effect of such an acidic treatment. As a result, it was found that if a predetermined type of carbonate salt and a predetermined type of azo dye are used in combination, in a predetermined ratio, it is possible to obtain a hair dye composition dyeing the hair with a brilliant color and reducing color change of dyed hair. It was also found that the hair dye composition is characterized by not only high solubility of an azo dye during production but also high resistance to acidic treatment after hair dyeing. Based on the findings, the present invention was accomplished.

<Component (A): Azo Dyes>

The hair dye composition of the present invention contains one or more azo dyes selected from the group consisting of the following (A-1), (A-2) and (A-3), as a component (A).

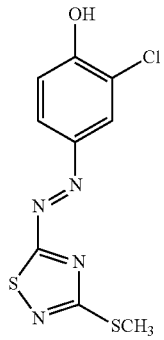

(A-1)

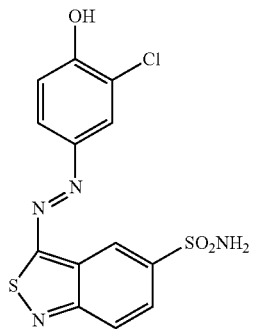

(A-2)

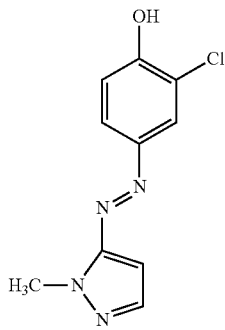

(A-3)

Note that, the pKa values of the azo dyes (A-1), (A-2) and (A-3) are 6.0, 6.0 and 7.5, respectively. Thus, in the hair dye composition of the present invention having pH (25° C.) of 7.5 to 12, almost 80% or more of these azo dyes are present in an anionic state where a proton(s) is dissociated. When a proton(s) dissociates, (A-1) displays red, (A-2) blue and (A-3) yellow.

The total content of the azo dye in a whole composition is, in order to increase hair-dyeability, suppress color transfer to e.g., cloths, and further improve solubility to a hair dye composition, preferably 0.01 mass % or more, further preferably 0.03 mass % or more, more preferably 0.05 mass % or more, further preferably 0.08 mass % or more and further preferably 0.1 mass % or more; and preferably 5 mass % or less, more preferably 3 mass % or less, further preferably 2.5 mass % or less, further preferably 1.5 mass % or less, further preferably 1 mass % or less and further preferably 0.5 mass % or less. Note that the hair dye composition of the present invention can use a dye other than the azo dyes (A-1), (A-2) and (A-3), in combination. However, in order not to affect dyeability of a component (A), it is preferable that the total content of the azo dyes (A-1), (A-2) and (A-3) is 1 mass % or more of in all the dyes, further 5 mass % or more and 100 mass % or less, further 10 mass % or more and 100 mass % or less and further 20 mass % or more and 100 mass % or less.

If a hair dye composition is a two-agent type or three-agent type composition, an azo dye as mentioned above may be contained in any one of a first agent, a second agent and a third agent. In view of the stability of the composition, the azo dye is preferably contained in a first agent or a third agent and more preferably contained in a first agent.

<Oxidation Dye>

In the case where the hair dye composition of the present invention is a two-agent type or three-agent type compositions, not only the azo dyes but also an oxidation dye can be added in the first agent. As a preferable oxidation dye for the hair dye composition of the present invention, a precursor and a coupler known in the art and used in conventional hair dyes can be used.

Examples of the precursor include para-phenylenediamine, toluene-2,5-diamine, 2-chloroparaphenylenediamine, para-aminophenol, para-methylaminophenol, ortho-aminophenol, 2,4-diaminophenol, N-phenyl-para-phenylenediamine and salts of these.

Examples of the coupler include meta-phenylenediamine, 2,4-diaminophenoxyethanol, meta-aminophenol, 2-methyl-5-aminophenol, 2-methyl-5-(2-hydroxyethylamino)phenol, resorcin, 1-naphthol, 1,5-dihydroxynaphthalene, hydroquinone and salts of these.

The precursors and couplers are individually used singly or in combination of two or more. The total content thereof in a whole composition is preferably set as long as the dyeability of the azo dyes is not affected. The total content is preferably 0.01 mass or more and more preferably 0.1 mass % or more; and preferably 5 mass % or less, more preferably 3 mass %, further preferably 2 mass % or less, further preferably 1 mass % or less and further preferably 0.5 mass or less.

<Direct Dye Other than Component (A)>

In the hair dye composition of the present invention, a direct dye other than the azo dyes (A-1), (A-2) and (A-3) can be further contained. In the case where the hair dye composition of the present invention is a two-agent type or three-agent type composition, a direct dye except azo dyes (A-1) (A-2) and (A-3) is preferably contained in a first agent. As the direct dye, an acid dye, a basic dye and a dispersive dye known in the art and available in hair dyes can be used.

Examples of the acid dye include Blue No. 1, Purple No. 401, Black No. 401, Orange No. 205, Red No. 227, Red No. 106, Yellow No. 203 and Acidic Orange 3. Examples of the basic dye include Basic Blue 99, Basic Blown 16, Basic Blown 17, Basic Red 76 and Basic yellow 57.

Examples of the direct dye other than the acid dyes and basic dyes include 2-nitro-p-phenylenediamine, 2-amino-6-chloro-4-nitrophenol, 3-nitro-p-hydroxyethylaminophenol, 4-nitro-o-phenylenediamine, 4-amino-3-nitrophenol, 4-hydroxypropylamino-3-nitrophenol, N,N-bis(2-hydroxyethyl)-2-nitro-p-phenylenediamine, dispersive Purple 1, dispersive Blue 1, dispersive Black 9, HC Blue 2, HC Orange 1, HC Red 1, HC Red 3, HC Yellow 2, HC Yellow 4 and HC Yellow 5.

These direct dyes other than the azo dyes (A-1), (A-2) and (A-3) can be used singly or in combination of two or more. The content thereof in a whole composition is preferably 0.001 mass % or more and more preferably 0.01 mass % or more; and preferably 5 mass % or less, more preferably 3 mass % or less, further preferably 2 mass % or less, further preferably 1 mass % or less and further preferably 0.5 mass % or less.

<Component (B): Carbonate Salt>

The hair dye composition of the present invention contains at least one type of carbonate salt selected from the group consisting of alkaline agents such as guanidine carbonate, guanidine hydrogen carbonate, sodium carbonate, sodium hydrogen carbonate, potassium carbonate, potassium hydrogen carbonate and lithium carbonate, as a component (B).

The total content of the component (B) in a whole composition is, in order to improve resistance to acidic treatment and solubility of a component (A) to a hair dye composition, preferably 0.01 mass % or more, more preferably 0.03 mass % or more, further preferably 0.05 mass % or more, further preferably 0.1 mass % or more and further preferably 0.3 mass % or more; and preferably 10 mass % or less, more preferably 9 mass % or less, further preferably 8 mass % or less, further preferably 6 mass % or less and further preferably 4 mass % or less.

A component (B) may be contained in either a first agent or a third agent when a hair dye composition is a two-agent type or three-agent type composition; however, in view of stability of a composition, a component (B) is preferably contained in a first agent.

The mass ratio of a component (B) to a component (A), (B)/(A), in a whole composition is, in order to improve resistance to acidic treatment and solubility of a component (A) to a hair dye composition, 1 or more, preferably 2 or more, more preferably 3 or more and further preferably 5 or more; and 100 or less, preferably 90 or less, more preferably 80 or less, further preferably 60 or less, further preferably 50 or less and further preferably 40 or less. Also in order to ensure high hair-dyeability, the mass ratio (B)/(A) is preferably 2 or more, more preferably 3 or more and further preferably 5 or more; and preferably 90 or less, more preferably 80 or less, further preferably 60 or less, further preferably 50 or less, further preferably 40 or less and further preferably 30 or less.

<pH>

The pH (25° C.) of the hair dye composition of the present invention during application is, in the case of a one-agent type hair dye, preferably 8 or more, more preferably 8.5 or more and further preferably 9 or more; and preferably 11.5 or less, more preferably further 11 or less and further preferably 10.5 or less.

In the case where the hair dye composition of the present invention is a two-agent type or three-agent type composition, the pH (25° C.) of a first agent is preferably 8 to 12 and the pH (25° C.) of a second agent is preferably 2 to 5. The pH (25° C.) of a mixture of first to third agents is, in view of hair dyeing effect and skin irritation, preferably 8 or more, more preferably 8.5 or more and further preferably 9 or more; and preferably 11.5 or less, more preferably 11 or less and further preferably 10.5 or less.

Note that, in the specification, the pH of a hair dye composition is a value measured at room temperature (25° C.) by a pH meter F-22 manufactured by Horiba, Ltd.

<Alkaline Agent Other than Component (B)>

To the hair dye composition of the present invention, an alkaline agent other than a carbonate salt serving as a component (B) can be further contained. If the hair dye composition of the present invention is a two-agent type or three-agent type composition, the alkaline agent is contained in a first agent. Examples of such an alkaline agent include ammonia and a salt thereof, sodium hydroxide, potassium hydroxide, an alkanolamine such as monoethanolamine, isopropanolamine, 2-amino-2-methylpropanol and 2-aminobutanol and a salt thereof; and an alkanediamine such as 1,3-propanediamine and a salt thereof. Of these alkaline agents, at least one member selected from the group consisting of ammonia and a salt thereof, monoethanolamine and a salt thereof and 2-amino-2-methyl propanol is preferable. Of these, 2-amino-2-methyl propanol is more preferable.

The alkaline agents other than a component (B) may be used in combination with two or more, a content thereof in a whole composition, is, in order produce a sufficient hair dyeing effect, preferably 0.01 mass % or more, further 0.05 mass % or more, further 0.1 mass % or more, further 0.2 mass % or more, further 0.5 mass % or more and further 1 mass % or more; and in order to reduce hair damage and scalp irritation, preferably 20 mass % or less, further 10 mass % or less, further 5 mass % or less, further 4 mass % or less and further preferably 3 mass % or less.

The mass ratio of a component (B) relative to an alkaline agent other than a component (B) [component (B)]/[alkaline agent other than component (B)] is, in order suppress color change by acidic treatment, preferably 0.005 or more, more preferably 0.01 or more, further preferably 0.05 or more, further preferably 0.3 or more, further preferably 0.5 or more and further preferably 1 or more; and preferably 3.5 or less, more preferably 3 or less, further preferably 2.5 or less, further preferably 2 or less and further preferably 1.5 or less.

<Surfactant>

To the hair dye composition of the present invention, a surfactant can be added. Examples of the surfactant include a cationic surfactant, a nonionic surfactant, an amphoteric surfactant and an anionic surfactant. Of these, in view of stability of a composition, an anionic surfactant and a nonionic surfactant are preferable.

Examples of the anionic surfactant include an alkylbenzene sulfonate salt, an alkyl or alkenyl ether sulfate salt, an alkyl or alkenyl sulfate salt, an olefin sulfonate salt, an alkane sulfonate salt, a saturated or unsaturated fatty acid salt, an alkyl or alkenyl ether carboxylate salt, an α-sulfo fatty acid salt, a N-acylamino acid salt, a phosphoric acid mono- or diester and a sulfosuccinic acid ester. Examples of the alkyl ether sulfate salt include polyoxyethylene alkyl ether sulfate salt. Of them, an alkyl sulfate salt, an alkyl ether sulfate salt, a saturated fatty acid salt and an alkyl ether carboxylate salt are preferable. Examples of the counter ions to the anionic groups of these anionic surfactants include alkali metal ions such as a sodium ion and a potassium ion; alkaline earth metal ions such as a calcium ion and a magnesium ion; an ammonium ion; and an alkanolamine salt having 1 to 3 alkanol groups having 2 or 3 carbon atoms (for example, monoethanolamine salt, diethanolamine salt, triethanolamine salt, triisopropanolamine salt).

As the cationic surfactant, in order to provide an excellent feel to the hair after hair dyeing, a monoalkyl trimethyl ammonium chloride, a dialkyl dimethyl ammonium chloride and monoalkyl trimethyl ammonium bromide are preferable. Of them, stearyl trimethyl ammonium chloride (steartrimonium chloride), cetyl trimethyl ammonium chloride (cetrimonium chloride), lauryl trimethyl ammonium chloride (lauryl trimonium chloride) are more preferable. These are preferably used as a mixture of two or more.

Examples of the nonionic surfactant include a polyoxyalkylene alkyl ether, a polyoxyalkylene alkenyl ether, a higher fatty acid sucrose ester, a polyglycerin fatty acid ester, a higher fatty acid mono- or di-ethanolamide, a polyoxyethylene hardened castor oil, a polyoxyethylene sorbitan fatty acid ester, a polyoxyethylene sorbitan fatty acid ester, an alkyl saccharide, an alkylamine oxide and an alkylamidoamine oxide. Of them, a polyoxyalkylene alkyl ether, a polyoxyethylene hardened castor oil and an alkyl saccharide are preferable, a polyoxyethylene alkyl (12 to 14) ether and an alkyl polyglucoside are more preferable.

Examples of the amphoteric surfactant include imidazoline, carbobetaine, amidobetaine, sulfobetaine, hydroxysulfobetaine and amidosulfobetaine. A betaine surfactant such as an alkyl dimethylaminoacetic acid betaine and a fatty acid amidopropylbetaine is more preferable and a fatty acid amidopropylbetaine is further preferable.

In the case where a hair dye composition is a two-agent type or three-agent type composition, a surfactant may be contained in any one of a first agent, a second agent and a third agent.

These surfactants can be used singly or in combination of two or more. The content thereof in a whole composition is, in order to obtain satisfactory texture and emulsification performance, preferably 0.01 mass %, more preferably 0.1 mass % or more, further preferably 0.2 mass % or more, further preferably 0.3 mass % or more and further preferably 0.5 mass % or more; and preferably 30 mass or less, more preferably 25 mass or less, further preferably 20 mass % or less, further preferably 10 mass less, further preferably 5 mass % or less, further preferably 3 mass or less and further preferably 1.5 mass or less.

<Cationic Polymer>

To the hair dye composition of the present invention, a cationic polymer can be contained. Examples of the cationic polymer include dimethyl diallyl ammonium salt-based copolymers such as a dimethyl diallyl ammonium chloride/acrylic acid copolymer, a dimethyl diallyl ammonium chloride/acrylamide copolymer and a dimethyl diallyl ammonium chloride/acrylamide/acrylic acid copolymer. Of them, a polymer containing a diallyl quaternary ammonium salt as a building block is preferably contained.

The polymer containing a diallyl quaternary ammonium salt as a building block is a polymer having a skeleton represented by the following formula (1) or (2).

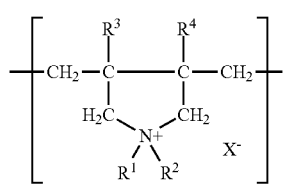

(1)

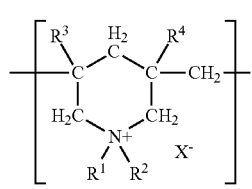

(2)

In the formula, $R^1$ and $R^2$ may be the same or different, each represent a hydrogen atom, or an alkyl group, an aryl group (e.g., phenyl group), a hydroxyalkyl group, an amidoalkyl group, a cyanoalkyl group, an alkoxyalkyl group or a carboalkoxyalkyl group having 1 to 18 carbon atoms; $R^3$ and $R^4$ may be the same or different, each represent a hydrogen atom, an alkyl group having 1 to 3 carbon atoms or a phenyl group; and $X^-$ represents an anion (e.g., a chloride ion, a bromide ion, an iodide ion, a sulfate anion, sulfonate anion, a methyl sulfate anion, a phosphate anion, nitrate anion).

The polymer containing a diallyl quaternary ammonium salt as a building block, in order to improve hair gloss, manageability and finger combability, contains preferably 85 to 100 mol %, more preferably 90 to 100 mol % and further preferably 95 to 100 mol % of a building block represented by the formula (4) or (5) in a molecule.

As the polymer containing a diallyl quaternary ammonium salt as a building block, a homopolymer of a diallyl quaternary ammonium salt and a diallyl quaternary ammonium salt/acrylic acid copolymer are preferable. Specific examples of the homopolymer of a diallyl quaternary ammonium salt include Merquat 100 (manufactured by Lubrizol Advanced Materials, Inc., charge density: 6.2 meq/g, weight-average molecular weight: 150,000). Specific examples of the diallyl quaternary ammonium salt/acrylic acid copolymer include Merquat 295 (manufactured by Lubrizol Advanced Materials, Inc., charge density: 6.0 meq/g, weight-average molecular weight: 190,000) and Merquat 280 (manufactured by Lubrizol Advanced Materials, Inc., charge density: 5.0 meq/g, weight-average molecular weight: 450,000).

As a polymer substance of a diallyl quaternary ammonium salt and acrylic acid, for example, a polymer represented by the following formula (3) or (4) is preferable.

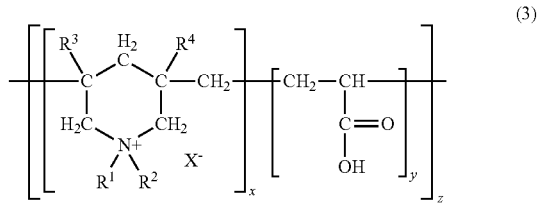

(3)

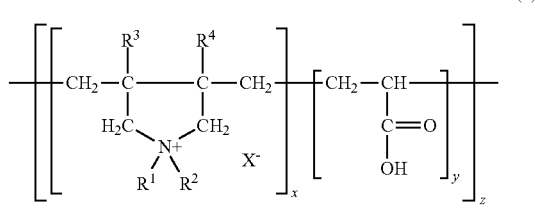

(4)

In each of the formulas, $R^1$, $R^2$, $R^3$, $R^4$ and $X^-$ are the same as defined above; x and y each represent an integer of 1 to 100; and z represents an integer of 150 to 8,000.

The ratio between x and y (x:y) is preferably 80:20, more preferably 90:10 and further preferably 95:5.

The weight-average molecular weight of a cationic polymer is, in order for the polymer to attach hair and rarely remove during hair-washing and rinsing; at the same time, to stabilize foams, preferably 10,000 or more, more preferably 50,000 or more and further preferably 100,000 or more; and in view of the satisfactory ejectability of foams, preferably 3,000,000 or less, more preferably 1,000,000 or less and further preferably 200,000 or less.

The weight-average molecular weight herein can be measured, for example, by gel permeation chromatography (GPC) in the following conditions.

Mobile phase: 50 mM LiBr, 1% $CH_3COOH$/ethanol:water=3:7
Column: TSK gel α-M (two column arranged in tandem)
Internal Standard: Polyethylene glycol The charge density of a cationic polymer is, in order improve hair-gloss, manageability and finger combability, preferably 5.0 meq/g or more, more preferably 5.5 meq/g or more and further preferably 6.1 meq/g or more; and, in view of stability of a composition, preferably 6.5 meq/g or less. Herein, the charge density of a cationic polymer refers to the mole number of cationic groups per polymer (1 g)×1000 (meq/g).

The content of a cationic polymer in a mixture is, in view of maintenance of effect, preferably 0.01 mass % or more, more preferably 0.05 mass % or more and further preferably 0.1 mass % or more; and preferably 5 mass % or less, more preferably 3 mass % or less, further preferably 1 mass % or less and further preferably 0.8 mass % or less. The cationic polymer may be contained in any one of a first agent, a second agent and a third agent in the case where a hair dye composition is a two-agent type or three-agent type composition.

<pH Adjuster>

The hair dye composition of the present invention can employ a pH adjuster such as an inorganic acid such as hydrochloric acid and phosphoric acid; an organic acid such as citric acid, glycolic acid, malic acid and lactic acid; a hydrochloride such as monoethanolamine hydrochloride; and a phosphate such as potassium dihydrogen phosphate and disodium hydrogen phosphate.

These pH adjusters may be contained in any one of a first agent, a second agent and a third agent in the case of a two-agent type or three-agent type hair dye composition. Furthermore, the content of a pH adjuster in a whole composition is, in order to produce a sufficient dyeing effect and reduce hair damage and scalp irritation, preferably 0.05 mass % or more, more preferably 0.1 mass % or more and further preferably 0.2 mass % or more; and preferably 15 mass % or less, more preferably 10 mass % or less, further preferably 5 mass % or less and further preferably 3 mass % or less.

<Hydrogen Peroxide>

In the case where the hair dye composition of the present invention is a two-agent type hair dye or three-agent type hair dye composition, hydrogen peroxide can be contained in a second agent. The content of hydrogen peroxide in a whole composition is, in order to produce a sufficient hair dyeing effect preferably 0.1 mass or more, further 0.5 mass % or more and further 1 mass % or more; and in order to reduce hair damage and scalp irritation, preferably 12 mass % or less, further 9 mass % or less, further 6 mass % or less and further preferably 4 mass % or less.

<Higher Alcohol>

To the hair dye composition of the present invention, a higher alcohol having 12 or more carbon atoms is preferably contained in order to improve texture and stability. The higher alcohol may be contained in any one of a first agent, a second agent and a third agent in the case where the hair dye composition of the present invention is a two-agent type or three-agent type composition.

As the higher alcohol, higher alcohols having 12 or more and further 16 or more carbon atoms; and 30 or less and further 22 or less carbon atoms are preferable. Specific examples thereof include myristyl alcohol, cetyl alcohol, stearyl alcohol, arachyl alcohol, behenyl alcohol, isostearyl alcohol, 2-octyldodecanol and oleyl alcohol.

The higher alcohols may be used in combination with two or more. The content thereof in a whole composition is, in view of viscosity and stability of a hair dye composition, preferably 3 mass % or more and further 4 mass % or more; and preferably 11 mass % or less and further 9 mass % or less.

<Organic Solvent>

The hair dye composition of the present invention may contain an organic solvent. Examples of the organic solvent include lower alkanols such as ethanol, 1-propanol and 2-propanol; aromatic alcohols such as benzyl alcohol, 2-benzyloxy ethanol and phenoxyethanol; polyols such as propylene glycol, 1,3-butanediol, diethylene glycol and glycerin; ether alcohols such as ethoxy ethanol, ethoxy diglycol and methoxy ethanol; N-alkyl pyrrolidones such as N-methylpyrrolidone and N-ethyl pyrrolidone; alkylene carbonates such as propylene carbonate; and lactones such as γ-valerolactone and γ-caprolactone.

These organic solvents can be used singly or in combination of two or more. The content thereof in a whole composition is preferably 0.1 mass % or more, more preferably 0.5 mass % or more and further preferably 1 mass % or more; and preferably 30 mass % or less, more preferably 20 mass % or less, further preferably 10 mass % or less and further preferably 5 mass % or less.

<Water-Soluble Polymer>

In the hair dye composition of the present invention, a water-soluble polymer can be contained in order to prevent dripping during application and deposition of dirt on e.g., the scalp. Note that, in the specification, the cationic polymer as mentioned above is not contained in the water-soluble polymer. Examples of the water-soluble polymer include gum Arabic, carrageenan, karaya gum, tragacanth gum, carob gum, quince seed (quince), casein, dextrin, gelatin, sodium pectate, sodium alginate, methylcellulose, ethylcellulose, carboxymethylcellulose (CMC), hydroxyethylcellulose, hydroxypropylcellulose, polyvinyl alcohol (PVA), polyvinyl methyl ether (PVM), polyvinylpyrrolidone (PVP), sodium polyacrylate, locust bean gum, guar gum, tamarind gum, dialkyl dimethyl ammonium cellulose sulfate, xanthan gum, modified xanthan gum, welan gum, Rhaball gum, gellan gum, a carboxyvinyl polymer, an acrylate-methacrylate copolymer, a methyl vinyl ether-maleic anhydride copolymer partially crosslinked with 1,9-decadiene, polyethylene glycol, magnesium aluminum silicate and bentonite. Of them, hydroxyethylcellulose, xanthan gum and modified xanthan gum are preferable.

These water-soluble polymers can be used singly or in combination of two or more. The content thereof in a whole composition is preferably 0.1 mass % or more and more preferably 0.5 mass % or more; and preferably 10 mass % or less and more preferably 5 mass % or less.

<Conditioning Component>

The hair dye composition of the present invention can contain a conditioning component suitable for applying to the hair. The conditioning component is a polymer or oil soluble or dispersible in a hair dye composition and deposits onto the hair when a hair dye composition is washed away or diluted with water and shampoo.

Example of the conditioning component suitable for use in the hair dye composition of the present invention include silicones (for example, silicone oil, cationic silicone, silicone gum, silicone resin), organic conditioning oils (for example, a hydrocarbon oil, a polyolefin, a fatty acid ester), aliphatic amides and polyalkylene glycols.

These conditioning components can be used singly or in combination of two or more. The content thereof in a whole composition is preferably 0.01 mass % or more, more preferably 0.05 mass % or more and further preferably 0.5 mass % or more; and preferably 20 mass % or less, more preferably 15 mass % or less and further preferably 5 mass % or less.

<Medium>

In the hair dye composition of the present invention, water is used as a medium. It is preferable that the content of water in a hair dye composition is 10 mass % or more, further 20 mass % or more, further 30 mass % or more and further 40 mass % or more and further 50 mass % or more; and 95 mass % or less, further 90 mass % or less and further 85 mass % or less.

<Other Optional Components>

In the hair dye composition of the present invention, other components used as normal cosmetic raw materials can be added other than the aforementioned components.

Such optional components can be added for the blending purpose of pearling, preservation, sequestering, stabilization, anti-oxidation, ultraviolet absorption, moisturization, product coloring and perfuming. Examples of the specific optional components include animal and vegetable fats and oils, higher fatty acids, protein hydrolysates, protein derivatives, amino acids, plant extracts, vitamins, dyes and fragrances.

<Dosage Form>

The hair dye composition of the present invention can be used as one-agent type, two-agent type, or three-agent type hair dye. The one-agent type hair dye composition consists of a single agent containing components (A) and (B). The two-agent type hair dye composition preferably consists of a first agent containing a component (A) and an alkali agent and a second agent containing hydrogen peroxide. The three-agent type hair dye composition preferably consists of a first agent containing an alkali agent, a second agent containing hydrogen peroxide and a third agent containing the component (A); or consists of a first agent containing a component (A) and an alkali agent, a second agent containing hydrogen peroxide and a third agent containing other components. As the third agent containing the other components, a powdery oxidizing agent formed of granules of a persulfate (e.g., ammonium persulfate, potassium persulfate, sodium persulfate) is preferably used for improving bleaching power.

Note that, in the present invention, "the whole composition" refers the entire composition to be applied to the hair-dye treatment. In the case of the two-agent type hair dye, a mixture prepared by mixing a first agent and a second agent is referred to and in the three-agent type hair dye, a mixture of a first agent, a second agent and a third agent is referred to.

The hair dye composition of the present invention can be used, for example, in the form of liquid, emulsion, cream, gel, paste and mousse and prepared in the form of aerosol. In these cases, it is desirable to control the viscosity of the whole composition so as to rarely drip out when the composition is applied to the hair. The viscosity of the whole composition (25° C.) is preferably 2,000 to 200,000 mPa·s, more preferably 4,000 to 150,000 mPa·s, further preferably 6,000 to 100,000 mPa·s and further preferably 8,000 to 80,000 mPa·s, as a measurement value obtained by a type-B rotational viscometer with a helical stand (model; digital viscometer TVB-10, Toki Sangyo Co., Ltd.) after the composition is rotated by use of rotor T-C at 10 rpm for one minute. Note that, in the case of a two-agent type or three-agent type composition, it is specified that the viscosity of the composition is determined 3 minutes after blending individual agents.

The hair dye composition of the present invention can be used in a form of foam by ejecting from a non-aerosol type foamer or shaking in a cup upon application to the hair. In this case, it is desirable to control the viscosity of the whole composition before foamed so as to avoid dripping when the composition is foamed and applied to the hair. The viscosity of the whole composition (25° C.) is preferably 1 to 800 mPa·s, more preferably 1 to 600 mPa·s, further preferably 1 to 500 mPa·s, further preferably 1 to 300 mPa·s as a measurement value measured by a type-B rotating viscometer (model; digital viscometer TV-10, Toki Sangyo Co., Ltd.) after the composition is rotated by use of rotor No. 1 at 30 rpm for one minute (note that when the viscosity excesses 160 mPa·s, a measurement value obtained after the composition is rotated at 12 rpm for one minute). Note that, in the case of a two-agent type or three-agent type composition, the viscosity of the composition is determined 3 minutes after blending individual agents.

<Method for Dyeing Hair>

Hair-dye treatment using the hair dye composition of the present invention may be performed, for example, by applying the hair dye composition of the present invention (after first to third agents are blended right before use in the case of a two-agent type or three-agent type composition), allowing to stand in a predetermined time, washing away the composition with water, and drying the hair. The application temperature is preferably 15 to 45° C. The application time is preferably for 1 to 60 minutes, further 5 to 45 minutes and further 10 to 30 minutes.

With respect to the aforementioned embodiment, preferable embodiments of the present invention will be further disclosed below.

<1> A hair dye composition comprising the following components (A) and (B), in which the mass ratio of a component (B) to a component (A), (B)/(A), in a whole composition is 1 or more and 100 or less and the pH (25° C.) during application is 7.5 to 12:

(A): one or more azo dyes selected from the group consisting of the following (A-1), (A-2) and (A-3):

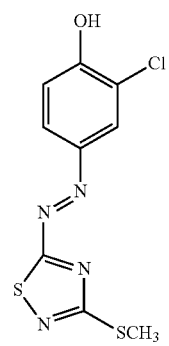

(A-1)

-continued

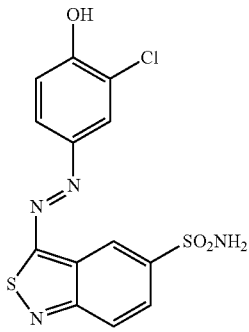

(A-2)

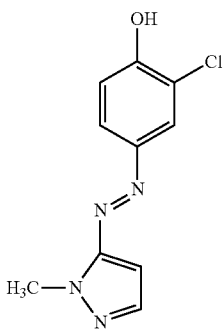

(A-3)

(B): at least one member selected from the group consisting of guanidine carbonate, guanidine hydrogen carbonate, sodium carbonate, sodium hydrogen carbonate, potassium carbonate, potassium hydrogen carbonate and lithium carbonate.

<2> The hair dye composition according to <1>, in which the content of the component (A) in the whole composition is preferably 0.01 mass % or more, more preferably 0.03 mass or more, further preferably 0.05 mass or more, further preferably 0.08 mass % or more and further preferably 0.1 mass % or more; and preferably 5 mass or less, more preferably 3 mass % or less, further preferably 2.5 mass % or less, further preferably 1.5 mass % or less, further preferably 1 mass % or less and further preferably 0.5 mass % or less.

<3> The hair dye composition according to <1> or <2>, in which the content of the component (B) in the whole composition is preferably 0.01 mass % or more, more preferably 0.03 mass % or more, further preferably 0.05 mass % or more, further preferably 0.1 mass % or more and further preferably 0.3 mass or more; and preferably 10 mass % or less, more preferably 9 mass % or less, further preferably 8 mass % or less, further preferably 6 mass % or less and further preferably 4 mass % or less.

<4> The hair dye composition according to any one of <1> to <3>, in which the mass ratio of the component (B) to the component (A), (B)/(A), in the whole composition is preferably 2 or more, more preferably 3 or more and further preferably 5 or more; and preferably 90 or less, more preferably 80 or less, further preferably 60 or less, further preferably 50 or less, further preferably 40 or less and further preferably 30 or less.

<5> The hair dye composition according to any one of <1> to <4>, preferably further comprising a surfactant.

<6> The hair dye composition according to <5>, in which the surfactant is preferably at least one member selected from the group consisting of an anionic surfactant, a cationic surfactant, a nonionic surfactant, and an amphoteric surfactant.

<7> The hair dye composition according to <5> or <6>, in which the content of the surfactant in the whole composition is preferably 0.01 mass %, more preferably 0.1 mass % or more, further preferably 0.2 mass % or more and further preferably 0.3 mass % or more; and preferably 30 mass % or less, more preferably 25 mass % or less, further preferably 20 mass % or less, further preferably 10 mass % or less, further preferably 5 mass % or less, further preferably 3 mass or less and further preferably 1.5 mass % or less.

<8> The hair dye composition according to <6> or <7>, in which the anionic surfactant is one or more member selected from the group consisting of an alkyl sulfate salt, an alkyl ether sulfate salt, a saturated fatty acid salt and an alkyl ether carboxylate salt.

<9> The hair dye composition according to any one of <1> to <8>, preferably further comprising a cationic polymer.

<10> The hair dye composition according to <9>, in which the cationic polymer is a polymer preferably containing a diallyl quaternary ammonium salt as a building block.

<11> The hair dye composition according to <9> or <10>, in which the weight-average molecular weight of the cationic polymer is preferably 10,000 or more, more preferably 50,000 or more and further preferably 100,000 or more; and preferably 3,000,000 or less, more preferably 1,000,000 or less and further preferably 200,000 or less.

<12> The hair dye composition according to any one of <9> to <11>, in which the content of the cationic polymer in the whole composition is preferably 0.01 mass % or more, more preferably 0.05 mass % or more and further preferably 0.1 mass % or more; and preferably 5 mass % or less, more preferably 3 mass % or less, further preferably 1 mass % or less and further preferably 0.8 mass % or less.

<13> The hair dye composition according to any one of <1> to <12>, preferably further comprising a higher alcohol having 12 or more carbon atoms.

<14> The hair dye composition according to <13>, in which the higher alcohol preferably has 16 or more carbon atoms; and preferably 30 or less carbon atoms and more preferably 22 or less carbon atoms.

<15> The hair dye composition according to <13> or <14>, in which the content of the higher alcohol is preferably 3 mass % or more and more preferably 4 mass % or more; and preferably 11 mass % or less and more preferably 9 mass % or less.

<16> The hair dye composition according to any one of <1> to <15>, preferably further comprising 2-amino-2-methylpropanol.

<17> The hair dye composition according to any one of <1> to <16>, in which the pH (25° C.) during application is preferably 8 or more, more preferably 8.5 or more and further preferably 9 or more; and preferably 11.5 or less, more preferably further 11 or less and further preferably 10.5 or less.

<18> A method for dyeing hair comprising applying the hair dye composition according to any one of <1> to <17> to hair, allowing the composition to stand for 1 to 60 minutes and washing away the composition.

<19> Use of the hair dye composition according to any one of <1> to <17> for dyeing hair.

EXAMPLES

Examples 1 to 8 and Comparative Examples 1 to 4

Hair dye compositions (one-agent type hair dye) having the compositions shown in Tables 3 and 4 were prepared by the following method. The obtained hair dye compositions were evaluated for dyeability, color of rinse water and dye solubility by the following methods. The results of these are all together shown in Tables 3 and 4.

<Method for Preparing Hair Dye Composition>

In water, a component (A), 2-amino-2-methylpropanol and propylene glycol were blended and thereafter a component (B) component was added (note that, a component (B) was not added in Comparative Example 4). The mixture was stirred at 60° C. for a predetermined time to prepare an Aqueous Solution 1. Subsequently, the dye solubility of Aqueous Solution 1 was checked. Separately, sodium laureth sulfate, cetearyl alcohol, myristyl alcohol, octyl dodecanol and oleyl alcohol were dissolved at 60° C. to prepare Oil Phase 1. Then, Oil Phase 1 was blended to Aqueous Solution 1. The mixture was stirred for a predetermined time and cooled to room temperature to obtain a hair dye composition.

<Dyeability>

The hair dye composition was applied to a hair tress of goat hair (1 g) in a bath ratio (composition:goat hair)=1:1 (mass ratio) and allowed to stand at 40° C. for 20 minutes, rinsed with water of about 40° C., washed with the shampoo shown in Table 1 and washed with water. Then, the hair conditioner shown in Table 2 was applied to the hair tress and rinsed with water of about 40° C. The resultant hair tress was wiped with towel and blow-dried.

The color of the obtained hair tress immediately after hair dyeing was measured by a color-difference meter (colorimeter CR-400, manufactured by Konica Minolta Sensing, Inc.) based on the CIE color system (L*, a*, b*). The difference from the color before dyeing was obtained in accordance the following expression and used as dyeability $\Delta E^*$. The larger $\Delta E^*$ means that the dyeability is more excellent.

$$\Delta E^* = \sqrt{(L_1^* - L_0^*)^2 + (a_1^* - a_0^*)^2 + (b_1^* - b_0^*)^2}$$

In the formula, $L^*_0$, $a^*_0$ and $b^*_0$ represent L*, a* and b* values of a hair tress before dyeing, respectively, and $L^*_1$, $a^*_1$ and $b^*_1$ are L*, a* and b* values of the hair tress immediately after dyeing, respectively.

TABLE 1

| Formulation of shampoo (pH 7) | Active amount (mass %) |
| --- | --- |
| Disodium edetate | 0.3 |
| Sodium benzoate | 0.5 |
| Lauramide DEA (diethanolamide)*1 | 1.5 |
| Sodium laureth sulfate*2 | 15.5 |
| Phosphoric acid | q.s. |
| Water | Balance |
| Total | 100 |

*1Aminon L-02, manufactured by Kao Corp.
*2EMAL 227-pH11 (W), manufactured by Kao Corp.

TABLE 2

| Hair conditioner formulation (pH 7) | Active amount (mass %) |
| --- | --- |
| Methylparaben | 0.1 |
| Cetearyl alcohol | 2.0 |
| Propylene glycol | 5.0 |
| Distearyl dimonium chloride*1 | 2.7 |

TABLE 2-continued

| Hair conditioner formulation (pH 7) | Active amount (mass %) |
| --- | --- |
| Steartrimonium chloride*2 | 0.8 |
| Water | Balance |
| Total | 100 |

*1QUARTAMIN D86P, manufactured by Kao Corp.
*2QUARTAMIN 86W, manufactured by Kao Corp.

<Resistance to Acidic Treatment (Color Change Due to Acidic Treatment)

A hair dye composition was applied to a hair tress of goat hair (1 g) in a bath ratio (composition:goat hair)=1:1 (mass ratio) and allowed to stand at 40° C. for 20 minutes, rinsed with water of about 40° C., washed with the shampoo shown in Table 1 and rinsed. Then, the hair conditioner shown in Table 2 was applied and rinsed with water of about 40° C. The resultant hair was wiped with towel and blow-dried.

The resultant goat hair was soaked in ion-exchange water controlled to have a bath ratio (ion exchanged water:goat hair)=1:1 (mass ratio) for 30 seconds. Thereafter, a commercially available acidic shampoo (ASIENCE shampoo; pH3.3, manufactured by Kao Corp) was applied to the hair tress in a bath ratio (composition:goat hair)=1:1 (mass ratio), allowed to stand at 40° C. for 5 minutes, rinsed with water of about 40° C., further a commercially available acidic hair conditioner (ASIENCE hair conditioner; pH3.3, manufactured by Kao Coip) was applied in a bath ratio (composition: goat hair)=1:1 (mass ratio), allowed to stand at 40° C. for 5 minutes and rinsed with water of about 40° C. The hair tress was wiped with towel and blow-dried.

The hair tress, before and after the acidic treatment, was measured by a color-difference meter (colorimeter CR-400, manufactured by Konica Minolta Sensing, Inc.) based on the CIE color system (L*, a*, b*). Then, a hue angle (h) was obtained in accordance with Formula 1 and difference $\Delta h_0$ in hue angle before and after the acidic treatment was obtained in accordance with Formula 2. The lower $\Delta h_0$ value means that resistance to acidic treatment is more excellent.

$$h = \tan^{-1}(b^*/a^*) \quad \text{Formula 1}$$

$$\Delta h_0 = \text{abs}(h_{r0} - h_{t0}) \quad \text{Formula 2}$$

In the formula, $h_{r0}$ and $h_{t0}$ respectively represent the value h of goat hair immediately after dyed without an acidic treatment and the value h of goat hair immediately after dyed with an acidic treatment.

<Dye Solubility>

The dye solubility of hair dye compositions was visually evaluated based on the criteria shown below during preparation of the hair dye compositions.

3: Dye is easily dissolved and no precipitate is present

2: No precipitate is present; however, time is required until a dye is dissolved 1: Precipitates are present

TABLE 3

|   | Active amount (mass %) | Example 1 | Example 2 | Example 3 | Example 4 | Example 5 | Example 6 | Comparative Example 1 | Comparative Example 2 | Comparative Example 3 | Comparative Example 4 |
|---|---|---|---|---|---|---|---|---|---|---|---|
| (A) | Azo dye (A-2) | 0.1 | 0.1 | 0.1 | 0.1 | 0.1 | 0.1 | 0.1 | 0.1 | 0.1 | 0.1 |
| (B) | Sodium hydrogen carbonate | 0.1 | 0.5 | 2 | 5 | 7.5 | 10 | 0.01 | 12 | 20 | — |
|   | 2-Amino-2-methylpropanol | 5 | 5 | 5 | 5 | 5 | 5 | 5 | 5 | 5 | 5 |
|   | Sodium laureth sulfate (*1) | 2.5 | 2.5 | 2.5 | 2.5 | 2.5 | 2.5 | 2.5 | 2.5 | 2.5 | 2.5 |
|   | Cetearyl alcohol | 5.6 | 5.6 | 5.6 | 5.6 | 5.6 | 5.6 | 5.6 | 5.6 | 5.6 | 5.6 |
|   | Myristyl alcohol | 5.6 | 5.6 | 5.6 | 5.6 | 5.6 | 5.6 | 5.6 | 5.6 | 5.6 | 5.6 |
|   | Octyldodecanol | 1.6 | 1.6 | 1.6 | 1.6 | 1.6 | 1.6 | 1.6 | 1.6 | 1.6 | 1.6 |
|   | Oleyl alcohol | 3.2 | 3.2 | 3.2 | 3.2 | 3.2 | 3.2 | 3.2 | 3.2 | 3.2 | 3.2 |
|   | Propylene glycol | 2.5 | 2.5 | 2.5 | 2.5 | 2.5 | 2.5 | 2.5 | 2.5 | 2.5 | 2.5 |
|   | Water | Balance | Balance | Balance | Balance | Balance | Balance | Balance | Balance | Balance | Balance |
|   | Total | 100 | 100 | 100 | 100 | 100 | 100 | 100 | 100 | 100 | 100 |
|   | pH (25° C.) | 10.28 | 10.25 | 10.11 | 9.75 | 9.75 | 9.35 | 10.29 | *2 | *2 | 10.29 |
|   | (B)/(A) | 1 | 5 | 20 | 50 | 75 | 100 | 0.1 | 120 | 200 | 0 |
| Evaluation | Dyeability (ΔE) | 60.7 | 65.2 | 64.3 | 58.1 | 56.1 | 52.4 | 60.1 | *2 | *2 | 59.6 |
|   | Color change by acidic treatment (Δh$_0$) | 6.3 | 3.0 | 1.7 | 0.3 | 0.3 | 0.7 | 11.3 | *2 | *2 | 27.0 |
|   | Dye solubility | 3 | 3 | 3 | 3 | 3 | 2 | 3 | 1 | 1 | 2 |

(*1): EMAL 227-pH11 (W), manufactured by Kao Corp.
*2: Evaluation was not made since the azo dye exhibited poor solubility to hair dye composition and remained undissolved.

TABLE 4

|   | Active amount (mass %) | Example 7 | Example 8 |
|---|---|---|---|
| (A) | Azo dye (A-2) | 0.05 | 0.05 |
| (B) | Guanidine carbonate | 2 | — |
|   | Potassium carbonate | — | 2 |
|   | 2-Amino-2-methylpropanol | 2 | 2 |
|   | Sodium laureth sulfate | 2.5 | 2.5 |
|   | Cetearyl alcohol | 5.6 | 5.6 |
|   | Myristyl alcohol | 5.6 | 5.6 |
|   | Octyldodecanol | 1.6 | 1.6 |
|   | Oleyl alcohol | 3.2 | 3.2 |
|   | Propylene glycol | 2.5 | 2.5 |
|   | Water | Balance | Balance |
|   | Total | 100 | 100 |
|   | pH (25° C.) | 8.99 | 8.79 |
|   | (B)/(A) | 40 | 40 |
| Evaluation | Dyeability (ΔE) | 48.3 | 44.6 |
|   | Color change by acidic treatment (Δh$_0$) | 5.3 | 5.5 |
|   | Dye solubility | 3 | 3 |

Examples 9 to 12

A first agent of each of the hair dye compositions (two-agent type hair dye) having the composition shown in Table 5 was prepared by the following method. Also, a second agent was prepared in accordance with a conventional method. A hair dye composition was prepared by mixing the first agent shown in Table 5 and the second agent in a ratio of 1:1 (mass ratio) and evaluated for dyeability, color of rinse water and dye solubility in the same manner as above. The evaluation results are all together shown in Table 5.

<Method for Preparing First Agent>

In water, a component (A), 2-amino-2-methylpropanol and propylene glycol were blended and then a component (B) was added. The mixture was stirred at 60° C. for a predetermined time to prepare an Aqueous Solution 1. Subsequently, the dye solubility of Aqueous Solution 1 was checked. Separately, sodium laureth sulfate, cetearyl alcohol, myristyl alcohol, octyl dodecanol and oleyl alcohol were dissolved at 60° C. to prepare Oil Phase 1. Then, Oil Phase 1 was blended to Aqueous Solution 1. The mixture was stirred for a predetermined time and cooled to room temperature. To this, polyquaternium-22 was added and the mixture was stirred for a predetermined time to obtain a first agent.

TABLE 5

|   |   | Active amount (mass %) | Example 9 | Example 10 | Example 11 | Example 12 |
|---|---|---|---|---|---|---|
| First agent | (A) | Azo dye (A-1) | 0.05 | 0.05 | 0.02 | 0.15 |
|   |   | Azo dye (A-3) | 0.1 | — | 0.08 | 0.3 |
|   |   | Azo dye (A-2) | 0.05 | 0.05 | — | 0.15 |
|   | (B) | Sodium hydrogen carbonate | 2 | 2 | 2 | 2 |
|   |   | 2-Amino-2-methylpropanol | 5 | 5 | 5 | 5 |
|   |   | Sodium laureth sulfate (*1) | 2.5 | 2.5 | 2.5 | 2.5 |
|   |   | Cetearyl alcohol | 5.6 | 5.6 | 5.6 | 5.6 |
|   |   | Myristyl alcohol | 5.6 | 5.6 | 5.6 | 5.6 |
|   |   | Octyldodecanol | 1.6 | 1.6 | 1.6 | 1.6 |
|   |   | Oleyl alcohol | 3.2 | 3.2 | 3.2 | 3.2 |
|   |   | Propylene glycol | 2.5 | 2.5 | 2.5 | 2.5 |
|   |   | Polyquaternium-22 (*2) | 0.2 | 0.2 | 0.2 | 0.2 |
|   |   | Water | Balance | Balance | Balance | Balance |
|   |   | Total | 100 | 100 | 100 | 100 |

TABLE 5-continued

|  |  | Example | | | |
|---|---|---|---|---|---|
|  | Active amount (mass %) | 9 | 10 | 11 | 12 |
| Second agent | Sodium lauryl sulfate | 0.19 | 0.19 | 0.19 | 0.19 |
|  | Cetearyl alcohol | 1.71 | 1.71 | 1.71 | 1.71 |
|  | Glycerin | 0.5 | 0.5 | 0.5 | 0.5 |
|  | Hydrogen peroxide solution | 5.7 | 5.7 | 5.7 | 5.7 |
|  | Etidronic acid | 0.054 | 0.054 | 0.054 | 0.054 |
|  | Salicylic acid | 0.02 | 0.02 | 0.02 | 0.02 |
|  | Disodium phosphate | 0.11 | 0.11 | 0.11 | 0.11 |
|  | Phosphoric acid | 0.24 | 0.24 | 0.24 | 0.24 |
|  | Water | Balance | Balance | Balance | Balance |
|  | Total | 100 | 100 | 100 | 100 |
|  | pH (25° C.) | 10.02 | 10.08 | 10.09 | 10.00 |
|  | (B)/(A) | 25 | 50 | 50 | 8.3 |
| Evaluation | Dyeability (ΔE) | 57.4 | 54.4 | 50.3 | 60.3 |
|  | Color change by acidic treatment (Δh$_0$) | 1.8 | 1.2 | 0.2 | 2.5 |
|  | Dye solubility of first agent | 3 | 3 | 3 | 3 |

(*1): EMAL 227-pH11 (W), manufactured by Kao Corp.
(*2): Merquat 280, manufactured by Japan LUBRIZOL

The invention claimed is:

1. A hair dye composition comprising the following components (A) and (B), wherein a mass ratio of a component (B) to a component (A), (B)/(A), in a whole composition is 1 to 60 and pH (25° C.) during application is 7.5 to 12:

(A): one or more azo dyes selected from the group consisting of the following (A-1), (A-2) and (A-3):

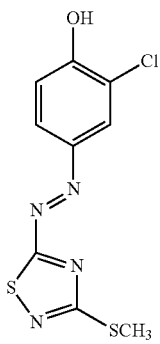

(A-1)

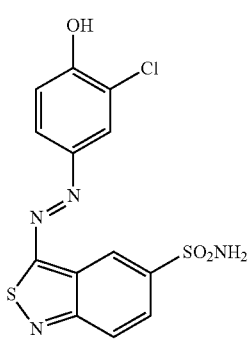

(A-2)

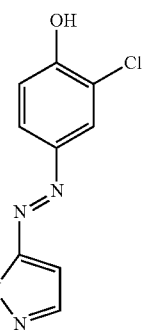

(A-3)

(B): at least one member selected from the group consisting of guanidine carbonate, guanidine hydrogen carbonate, sodium carbonate, sodium hydrogen carbonate, potassium carbonate, potassium hydrogen carbonate and lithium carbonate.

2. The hair dye composition according to claim 1, wherein a content of the component (A) in the whole composition is 0.01 mass % or more and 5 mass % or less.

3. The hair dye composition according to claim 1, wherein a content of the component (B) in the whole composition is 0.01 mass % or more and 10 mass % or less.

4. The hair dye composition according to claim 1, further comprising a surfactant.

5. The hair dye composition according to claim 4, wherein the surfactant is at least one member selected from the group consisting of an anionic surfactant, a cationic surfactant, a nonionic surfactant, and an amphoteric surfactant.

6. The hair dye composition according to claim 4, wherein a content of the surfactant in the whole composition is 0.01 mass % or more and 30 mass % or less.

7. The hair dye composition according to claim 5, wherein the anionic surfactant is one or more member selected from the group consisting of an alkyl sulfate salt, an alkyl ether sulfate salt, a saturated fatty acid salt, and an alkyl ether carboxylate salt.

8. The hair dye composition according to claim 1, further comprising a cationic polymer.

9. The hair dye composition according to claim 8, wherein the cationic polymer is a polymer containing a diallyl quaternary ammonium salt as a building block.

10. The hair dye composition according to claim 8, wherein a content of the cationic polymer in the whole composition is 0.01 mass % or more and 5 mass % or less.

11. The hair dye composition according to claim 1, further comprising a higher alcohol having 12 or more carbon atoms.

12. The hair dye composition according to claim 11, wherein a content of the higher alcohol is 3 mass % or more and 11 mass % or less.

13. The hair dye composition according to claim 1, further comprising 2-amino-2-methylpropanol.

14. A method for dyeing hair, comprising:
applying the hair dye composition according to claim 1, allowing the composition to stand for 1 to 60 minutes and washing away the composition.

15. A hair dye composition comprising the following components (A) and (B), wherein a mass ratio of a component (B) to a component (A), (B)/(A), in a whole composition is 5 to 60 and pH (25° C.) during application is 7.5 to 12:

(A): one or more azo dyes selected from the group consisting of the following (A-1), (A-2) and (A-3):

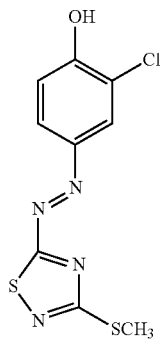

(A-1)

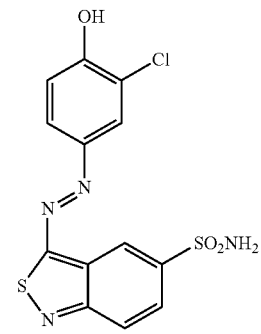

(A-2)

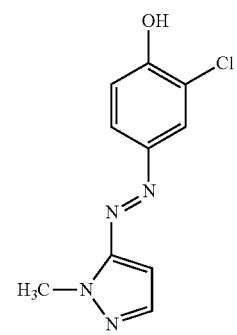

(A-3)

(B): at least one member selected from the group consisting of guanidine carbonate, guanidine hydrogen carbonate, sodium carbonate, sodium hydrogen carbonate, potassium carbonate, potassium hydrogen carbonate and lithium carbonate.

16. The hair dye composition according to claim 1, wherein the mass ratio of a component (B) to a component (A), (B)/(A), in a whole composition is 20 to 60 and pH (25° C.) during application is 7.5 to 12.

17. The hair dye composition according to claim 15, wherein (A) is (A-2).

18. The hair dye composition according to claim 1, wherein (A) is (A-2).

* * * * *